US006737504B2

(12) United States Patent
Freund et al.

(10) Patent No.: US 6,737,504 B2
(45) Date of Patent: May 18, 2004

(54) SYNTHESIS OF SUBSTITUTED POLY (ANILINE)S

(75) Inventors: Michael S. Freund, Winnipeg (CA); Eiichi Shoji, Fukui (JP)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/208,083

(22) Filed: Jul. 29, 2002

(65) Prior Publication Data

US 2003/0055212 A1 Mar. 20, 2003

Related U.S. Application Data

(60) Provisional application No. 60/308,723, filed on Jul. 30, 2001.

(51) Int. Cl.$^7$ .......................... C08G 73/00; C08G 79/08
(52) U.S. Cl. ........................ 528/422; 528/394; 528/489; 528/490; 525/540; 252/500
(58) Field of Search ................................. 528/394, 422, 528/489, 490; 525/540; 252/500

(56) References Cited

U.S. PATENT DOCUMENTS

| | | | | | |
|---|---|---|---|---|---|
| 5,147,913 | A | * | 9/1992 | MacDiarmid et al. | ...... 524/104 |
| 6,140,462 | A | * | 10/2000 | Angelopoulos et al. | ...... 528/422 |
| 6,193,909 | B1 | * | 2/2001 | Angelopoulos et al. | ...... 252/500 |
| 6,235,871 | B1 | * | 5/2001 | Singer et al. | ................ 528/485 |
| 6,265,532 | B1 | * | 7/2001 | Nicolau et al. | .............. 528/422 |
| 6,380,346 | B1 | * | 4/2002 | Han | ............................ 528/210 |

OTHER PUBLICATIONS

"New Boronic–Acid– and Boronate–Substituted Aromatic Compounds as Precursors of Fluoride–Responsive Conjugated Polymer Films", Mael Nicolas et al European Journal of Organic Chemistry, 2000, pp. 1703–1710.*
Badone et al. (1997), "Highly Efficient Palladium–Catalyzed Boronic Acid Coupling Reactions in Water: Scope and Limitations," *J. Org. Chem.* 62(21):7170–7173.
Bardero et al. (1989), "Formation of a Novel Electroactive Film by Electropolymerization of Ortho–Aminophenol. Study of Its Chemical Structure and Formation Mechanism. Electropolymerization of Analogous Compounds," *J. Electroanal. Chem.* 263:333–352.
Bardero et al. (1990), "Electrochemical Properties of Poly–Ortho–Aminophenol Modified electrodes in Aqueous Acid Solutions," *J. Electroanal. Chem.* 291:81–101.
Cohen et al. (1966), "The Production of Organocopper Intermediates from Radicals in the Reactions of Aromatic Halides and Diazonium Ions with Cuprous Benzoate. New Synthetic Methods for Aryl Benzoates," *Journal of the American Chemical Society* 88(19):4521–4522.
Cohen et al. (1974), "Organocopper Intermediates in the Exchange Reaction of Aryl Halides with Salts of Copper(I). The Possible Role of Copper(III)," *Tetrahedron Letters* 40:3555–3558.

Dao et al. (1989), "Synthesis and Characterization of Substituted Poly(Anilines)," *Synthetic Metals* 29:E377–E382.
Goncalves et al. (2000), "Electrochemical Oxidation of o–Aminophenol in Aqueous Acidic Medium: Formation of Film and Soluble Products," *Journal of Electroanalytical Chemistry* 487:90–99.
Herradura et al. (2000), "Copper–Mediated Cross–Coupling of Aryl Boronic Acids and Alkyl Thiols," *Organic Letters* 2(14):2019–2022.
Kuivila et al. (1954), "Areneboronates from Diols and Polyols," *Journal of Organic Chemistry* 19:780–783.
Kunimura et al. (1988), Preparation of Thin Polymeric Films on Electrode Surfaces by Electropolymerization of o–Aminophenol, *Macromolecules* 21(4):894–900.
Pringsheim et al. (1997), "Optical Sensing of pH Using Thin Films of Substituted Polyanilines," *Analytica Chimica Acta* 357:247–252.
Nesmeyanow et al. (1960), "Synthese von Ferrocenderivaten Mittels Bor– und Halogensubstituierter Ferrocene," *Chem. Ber.* 93:2717–2729.
Ohsaka et al. (1988), "Electrode Kinetics of Poly (o–Amionophenol) Film Prepared by Electro–Oxidative Polymerization of o–Aminophenol and Its Electrochromic Properties," *Electrochimica Acta* 33(5):639–645.
Salzbrunn et al. (2000), "Regioselective Nitration of Aryl-boronic Acids," *Synlett* 10:1485–1487.
Savarin et al. (2000), "Thiol Ester–Boronic Acid Cross–Coupling, Catalysis Using Alkylative Activation of the Palladium Thiolate Intermediate," *Organic Letters* 2(20):3229–3231.
Savarin et al. (2001), "Substituted Alkyne Synthesis Under Nonbasic Conditions: Copper Carboxylate–Mediated, Palladium–Catalyzed Thioalkyne–Boronic Acid Cross–Coupling," *Organic Letters* 3(1):91–93.
Simon et al. (2001), "Regioselective, Conversion of Aryl-boronic Acids to Phenols and Subsequent Coupling to Symmetrical Diaryl Ethers," *J. Org. Chem.* 66(2):633–634.
Snauwaert et al. (1986), "Electronic Structure of Polyanilines: An XPS Study of Electrochemically Prepared Compounds," *Synthetic Metals* 16:245–255.
Suzuki (1991), "Synthetic Studies via the Cross–Coupling Reaction of Organoboron Derivatives with Organic Halides," *Pure & Appl. Chem.* 63(3):419–422.

(List continued on next page.)

*Primary Examiner*—P. Hampton-Hightower
(74) *Attorney, Agent, or Firm*—Reed & Eberle LLP; Shelley P. Eberle

(57) ABSTRACT

A method for preparing a wide range of substituted poly (aniline)s from a single precursor is described. The method uses a variety of reactions, including a boron activation/electrophilic displacement reaction resulting in ipso-substitution. The ability to tune the properties of poly (aniline) through the generation of new structures is useful in numerous fields ranging from polymer-based electronics to sensors.

40 Claims, No Drawings

OTHER PUBLICATIONS

Thiebes et al. (1998), "Mild Preparation of Haloarenes by Ipso–Substitution of Arylboronic Acids with N–Halosuccinimides," *Synlett*, pp. 141–142.

Tsuchida et al. (1993), "Synthetic Route to Poly(Sulfonyl–1, 4–Phenylenethio–1,4–Phenylene) via a Poly(Sulfonium Cation)," *Macromolecules* 26:7389–7390.

Vogels et al. (1999), "Reactions of Aminoboron Compounds with Palladium and Platinum Complexes," *Can. J. Chem.* 77:1196–1207.

Zhang et al. (1994), "Synthesis and Electrochromic Properties of Poly–o–Aminophenol," *Journal of Electroanalytical Chemistry* 373:115–121.

Shoji et al. (2001), "A New Precursor to Substituted Poly(aniline)s," *Langmuir* 17(23):7183–7185 (abstract only).

* cited by examiner

SYNTHESIS OF SUBSTITUTED POLY(ANILINE)S

CROSS REFERENCE To RELATED APPLICATIONS

This application claims priority under 35 U.S.C. §119(e)(1) to U.S. Provisional Application Ser. No. 60/308,723, filed Jul. 30, 2001.

FIELD OF THE INVENTION

This invention relates to methods of synthesizing substituted poly(aniline)s. More particularly, the invention relates to the use of poly(aniline boronic acid) as a precursor in these methods.

BACKGROUND OF THE INVENTION

Substituted poly(aniline)s are of great interest for a variety of applications ranging from polymer-based electronics to sensors, as well as numerous electrocatalytic applications. As a result, there has been considerable interest in developing new synthetic approaches for their production.

Typically, these substituted polymers are generated by the oxidative polymerization of the corresponding monomer. See, for example, Pringsheim, et al., *Anal. Chim. Acta* 357:247–252 (1997). However, in many cases the desired moiety is either too difficult to oxidize or is sensitive to oxidative or acidic conditions. One alternative method involves the use of a monomer containing a reactive substituent group to synthesize a precursor polymer that subsequently can be modified to form the desired structure Tsuchida, et al., *Macromolecules* 26, 7389–7390 (1993).

Boronic acid groups are reactive and provide a versatile chemical precursor for various transformations with isolated yields typically greater than 90%. Examples of such transformation reactions are illustrated in Schemes 1–9.

Aromatic boronic acid groups can be used for transformations via ipso-hydroxylation under mild conditions (Simon, et al., *J. Org. Chem.* 66:633–634 (2001)). A boron activation/electrophilic displacement mechanism giving this ipso-substitution has been proposed, as shown in the following Scheme 1:

Scheme 1

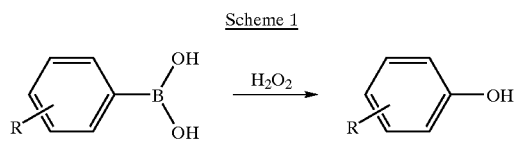

Simon also describes the regioselective oxidation of arylboronic acids to phenols and their one-pot conversions to symmetrical diaryl ethers under mild conditions (room temperature).

Aromatic boronic acid groups can be used for transformations via ipso-halogenation under mild conditions ((i) Nesmeyanov, et al., *Chem. Ber.* 93:2717 (1960); and (ii) Kuivila, et al., *J. Org. Chem.* 76:2679–2682 (1954) and Thiebes, et al., *Synlett* 141–142 (1998)). A boron activation/electrophilic displacement mechanism giving this ipso-substitution has been proposed, as shown in the following Scheme 2:

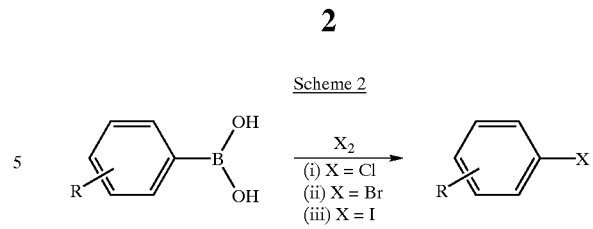

Aromatic boronic acid groups can be used for copper-mediated cross-coupling with alkyl thiols (Herradura, et al., *Org. Lett.* 2(14):2019–2022 (2000)), as shown in the following Scheme 3:

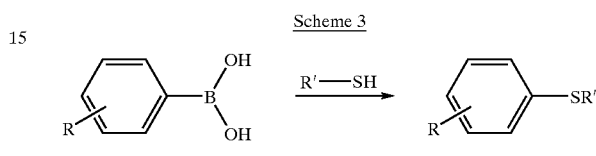

Aromatic boronic acid groups can be used for a transmetallation reaction, as shown in the following Scheme 4:

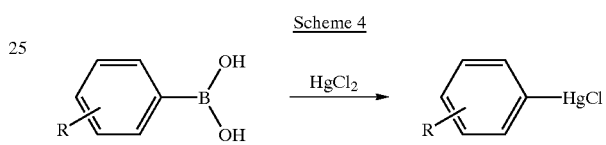

Aromatic boronic acid groups can be used for copper carboxylate-mediated, catalyzed thioalkyne cross-coupling reactions to produce substituted alkynes (Savarin, et al., *Org. Lett.* 3(1):91–93 (2001)), as shown in the following Scheme 5:

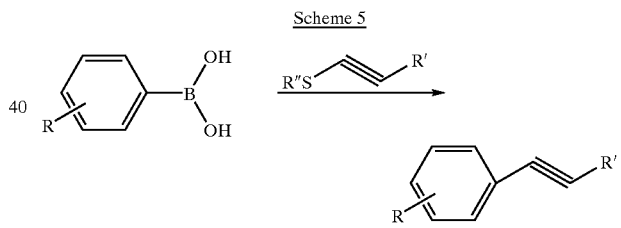

Aromatic boronic acid groups can be used for cross-coupling reactions with thiol avarin, et al., *Org. Lett.* 2(20):3229–3231 (2000)), as shown in the following Scheme 6:

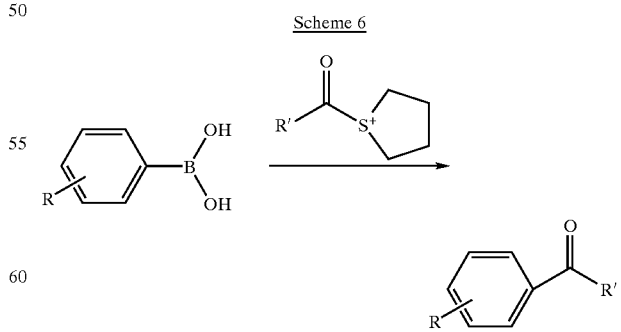

Aromatic boronic acid groups can also be used in a reaction that is widely known as the Suzuki cross-coupling reaction. This coupling reaction is an extremely powerful route to produce C—C bonds under mild conditions (Suzuki, *Pure Appl. Chem.* 63:419 (1991) and Badone, et al. *J. Org. Chem.* 62:7170–7173 (1997)), as shown in the following Scheme 7:

Scheme 7

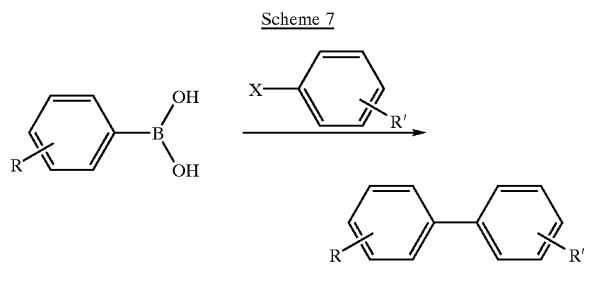

Aromatic boronic acid groups can be used for the synthesis of organoborane compounds (Vogels, et al., *Can. J Chem.* 77(7):1196–1207 (1999)), as shown in the following 8:

Scheme 8

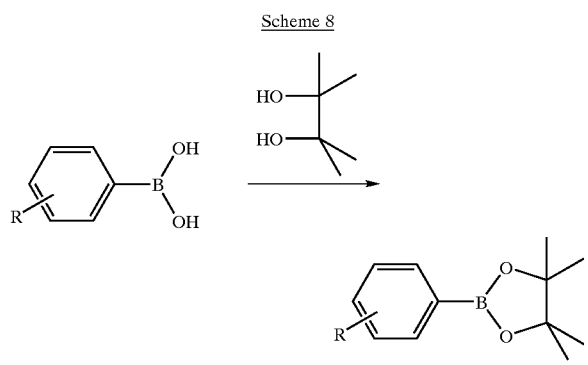

Aromatic boronic acid groups can be used for transformations via ipso-nitration under mild conditions (Salzbrunn, et al., *Synlett* 1485–1487 (2000)). A boron activation/electrophilic displacement mechanism giving this ipso-substitution has been proposed, as shown in Scheme 9.

Scheme 9

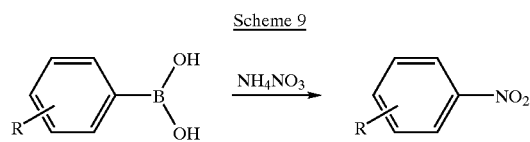

In spite of the advances in the art, there continues to be a need to develop synthetic strategies for the synthesis of this useful class of compounds. For example, conventional methods of producing diaryl ethers such as Ulman reactions require activated substrates (Patai, *The Chemistry of the Hydroxyl Group*, Part 1, Wiley, New York, 1971) and high temperature conditions (140–160° C., Cohen, et al., *Tetrahedron Lett.* 3555–3558 (1974), and Cohen, et al., *J. Am. Chem. Soc.* 88, 4521–4522 (1966)). Accordingly, it is desirable to develop synthetic routes that avoid the need for such activated substrates and high temperatures.

Other problems associated with current methodologies relate to side reactions that occur, resulting in a variety of products that can result from a single reaction. An important example of a substituted poly(aniline) whose structure is complicated by side reactions occurring during oxidative polymerization of its monomer 1, is poly-(hydroxyaniline) 4, as shown in the scheme below:

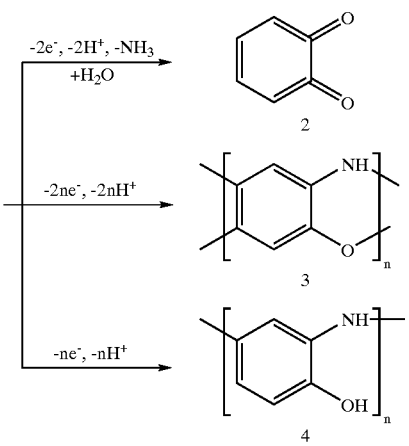

The structure of the polymer produced by the electrochemical oxidation of 1 is complicated due to the similar oxidative reactivity of both —$NH_2$ and —OH groups as well as the loss of —$NH_2$ to form 2. Several reports exist in the literature regarding whether a ladder 3 or linear 4 polymer is formed (Kunimura, et al., *Macromolecules* 21:894–900 (1988); Ohsaka, et al., *Electrochim. Acta* 33:639–645 (1988); Barbero, et al., *J. Electroanal. Chem.* 263:333–352 (1989); Barbero, et al., *J. Electroanal. Chem.* 291:81–101 (1990); Goncalves, et al., J. Electroanal. Chem. 487:90–99 (2000); and Zhang, et al. *J. Electroanal. Chem.* 373:115–121 (1994)). Evidence has been presented that suggests both forms are possible. Accordingly, it is desirable to develop synthetic routes that provide for the exclusive generation of the desired product, for example compound 4.

Additional problems associated with current methodologies relate to the synthesis of compounds such as halogen-substituted poly(aniline)s, which are difficult to synthesize using standard approaches (Dao, et al., *Synth. Met.* 29:E377–382 (1989) and Pringsheim, et al., *Anal. Chim. Acta* 357:247–252 (1997)). For example, during standard oxidative polymerization conditions, halogen-substituted anilines have been known to undergo elimination, resulting in the loss of a significant amount of halogen (4–48% for Cl and Br) in the resulting polymer (Snauwaert, at el., *Synth. Met.* 16:245–255 (1986)).

The present invention addresses these needs by using poly(aniline boronic acid) as the precursor in the synthesis of a wide range of substituted poly(aniline)s.

SUMMARY OF THE INVENTION

One aspect of the invention relates to a method of synthesizing a substituted poly(aniline), comprising reacting poly(aniline boronic acid) with a reagent to produce a substituted poly(aniline) of formula I:

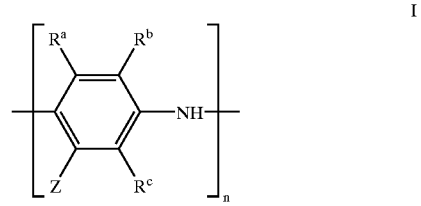

where n is an integer within the range of about 1–10,000,000; $R^a$, $R^b$ and $R^c$ are independently selected from the group consisting of —H, —$B(OH)_2$, alkyl, cycloalkyl, cycloheteroalkyl, aryl, heteroaryl and silyl; and Z is a substituent produced by the reaction of the reagent and the boronic acid substituent.

Another aspect of the invention pertains to a method of synthesizing a substituted poly(aniline), comprising: reacting poly(aniline 3-boronic acid) with at least one reagent selected from the group consisting of oxidation reagents, ipso-substitution reagents, and cross-coupling reagents; to produce a substituted poly(aniline) of formula I, where n is an integer within the range of about 1–10,000,000; $R^a$, $R^b$ and $R^c$ are independently selected from the group consisting of —H, —B(OH)$_2$, alkyl, cycloalkyl, cycloheteroalkyl, aryl, heteroaryl and silyl; and Z is a substituent produced by the reaction of the reagent and the boronic acid substituent.

Yet another aspect of the invention relates to a method of synthesizing a substituted poly(aniline) comprising reacting poly(aniline boronic acid) with at least one reagent selected from the group consisting of oxidation reagents, ipso-substitution reagents, and cross-coupling reagents; stopping the reaction before all of the boronic acid substituents in the poly(aniline boronic acid) undergo oxidation, substitution or cross-coupling; to produce a substituted poly(aniline) of formula I':

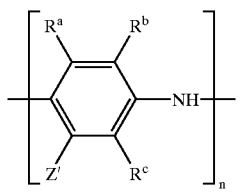

where n is an integer within the range of about 1–10,000,000; $R^a$, $R^b$ and $R^c$ are independently selected from the group consisting of —H, alkyl, —B(OH)$_2$, cycloalkyl, cycloheteroalkyl, aryl, heteroaryl and silyl; and wherein each Z' is independently selected from the group consisting of —B(OH)$_2$ and substituents produced by the reaction of the reagent and the boronic acid substituent, with the proviso that at least one Z' substituent is a substituent produced by the reaction of the reagent and the boronic acid substituent.

Still another aspect of the invention pertains to a method of synthesizing a substituted poly(aniline) comprising: reacting poly(aniline boronic acid) with at least one reagent selected from the group consisting of oxidation reagents, ipso-substitution reagents, and cross-coupling reagents; to produce a substituted poly(aniline) of formula I:

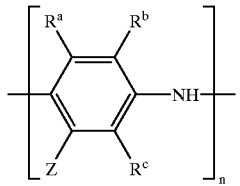

where n is an integer within the range of about 1–10,000,000; $R^a$, $R^b$ and $R^c$ are independently selected from the group consisting of —H, alkyl, —B(OH)$_2$, cycloalkyl, cycloheteroalkyl, aryl, heteroaryl and silyl; and wherein each Z is the same or different and is a substituent produced by the reaction of the reagent and the boronic acid substituent.

DETAILED DESCRIPTION OF THE INVENTION

The present invention provides a method for preparing a wide variety of substituted poly(aniline)s from a single precursor, poly(aniline boronic acid). Numerous reactions, including a boron activation/electrophilic displacement reaction that results in an ipso-substitution, provides for the generation of many possible structures such as poly (hydroxyaniline) and halogenated poly(aniline)s.

Before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. The following description of the preferred embodiments and examples are provided by way of explanation and illustration. As such, they are not to be viewed as limiting the scope of the invention as defined by the claims. Additionally, when examples are given, they are intended to be exemplary only and not to be restrictive. For example, when an example is said to "include" a specific feature, that is intended to imply that it may have that feature but not that such examples are limited to those that include that feature.

It must be noted that, as used in this specification and the appended claims, the singular forms "a", "an" and "the" include plural referents unless the context clearly dictates otherwise. Thus, for example, reference to "a reagent" includes a mixture of two or more such reagents, and the like.

In describing and claiming the present invention, the following terminology will be used in accordance with the definitions set out below.

"Alkyl" is used herein to refer to a branched or unbranched saturated hydrocarbon group typically although not necessarily containing about 1–24 carbon atoms, unless indicated otherwise. Exemplary alkyl groups include methyl, ethyl, n-propyl, isopropyl, n-butyl, isobutyl, t-butyl, n-amyl, isoamyl, n-hexyl, n-heptyl, n-octyl, n-decyl, hexyloctyl, tetradecyl, hexadecyl, eicosyl, tetracosyl, and the like, as well as cycloalkyl groups such as cyclopropyl, cyclobutyl, cyclopentyl, cyclohexyl, cycloheptyl, cyclooctyl and the like. Generally, although again not necessarily, alkyl groups herein contain about 1–12 carbon atoms. The term "lower alkyl" refers to an alkyl group of 1–6 carbon atoms, preferably 1–4 carbon atoms. In addition, the alkyl group can be substituted at one or more positions. Exemplary substituents include but are not limited to hydroxyl, boronic acid, cyano, alkoxy, =O, =S, —NO$_2$, halo, heteroalkyl, amine, thioether, —SH, and aryl. Accordingly, if not otherwise indicated, the term "alkyl" includes linear, branched, unsubstituted, substituted, and/or heteroatom-containing alkyl groups. The term "cycloalkyl" typically refers to a stable 3-to 7 membered monocyclic or 7-to 10-membered polycyclic ring which is saturated or partially unsaturated (e.g., containing one or more double bonds). Cycloheteroalkyls are cycloalkyls that contain one or more heteroatoms, and are typically stable 3-to 7 membered monocyclic or 7-to 10-membered polycyclic rings which are saturated or partially unsaturated and contain 1–4 heteroatoms (N, O, S, P or Si). Cycloalkyls and cycloheteroalkyls can be unsubstituted or substituted, where the substitutions can be on a carbon or a heteroatom if the resulting compound is stable. For example, any amino group contained within the heterocycloalkyl group can be a primary, secondary or tertiary amine, as long as the structure is stable.

"Aryl" is used herein to mean an aromatic substituent containing a single aromatic ring (e.g., phenyl) or multiple aromatic rings that are fused together (e.g., naphthyl or biphenyl), directly linked, or indirectly linked (such that the different aromatic rings are bound to a common group such as a methylene or ethylene moiety). Typically, the aryl group comprises from 5–14 carbon atoms. Preferred aryl groups contain one aromatic ring or two fused or linked aromatic rings, e.g., phenyl, naphthyl, biphenyl, diphenylether, diphenylamine, benzophenone, and the like. The aryl moiety may be independently substituted with one or more substituent groups, typically 1–3 substituents, including boronic acid, =O, —OH, —COOH, —CH$_2$—SO$_2$-phenyl, —C$_{1-6}$alkyl, —O—C$_{1-6}$alkyl, —C(O)—C$_{1-4}$alkyl, —(CH$_2$)$_{0-2}$—C(O)—O—C$_{1-4}$alkyl, cycloalkyl,—C$_{1-6}$alkoxy, halo, nitro, amino, alkylamino, dialkylamino, —C(O)—N(C$_{1-4}$alkyl)$_2$, —NH—C(O)—C$_{1-4}$alkyl, —C(O)—NH$_2$, —SO$_2$—NH$_2$, trifluoromethyl, cyano, aryl, benzyl, —O-aryl and —S-aryl. Thus, the term "aryl" includes unsubstituted and substituted aryl groups. The term "heteroaryl" refer to aryl, as defined above, in which at least one carbon atom, typically 1–3 carbon atoms, is replaced with a heteroatom (N, O, S, P or Si). The heteroaryl can have the heteroatoms within a single ring, (e.g., such as pyridyl, imidazolyl, thiazolyl, pyrimidine, oxazolyl, and the like), or within two rings (e.g., indolyl, quinolinyl, benzofuranyl, and the like). As with aryl, the term "heteroaryl" is intended to include both unsubstituted and substituted heteroaryl groups. The substitutions can be on a carbon or a heteroatom if the resulting compound is stable. For example, any amino group contained within the heteroaryl group can be a primary, secondary or tertiary amine, as long as the structure is stable.

"Silyl" is used herein to mean a silyl group (—SiH$_3$) or derivative thereof. The term silyl can thus be represented by the formula —SiR$_3$, where each R group is independently H, alkyl, cycloalkyl, cycloheteroalkyl, aryl or heteroaryl, an example of which is trimethylsilyl.

In its simplest form, the poly(aniline 3-boronic acid) (PABA) 6 precursor is readily synthesized by electrochemical polymerization of 3-aminophenylboronic acid in the presence of fluoride, as shown in Example 1.

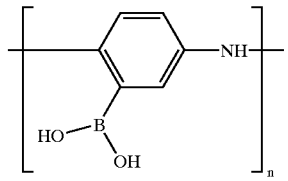

6

Electrochemical methodologies are described in Shoji, et al., *J. Am. Chem. Soc.* 123:3383–3384 (2001) and Nicolas, et al., *Eur. J. Org. Chem.* 9:1703–1710 (2000), while the actual PABA synthesis is described in Valeur, et al., *J. Phys. Chem.* 96:6545–6549 (1992). The resulting poly(aniline 3-boronic acid) polymer exhibits conductivities and redox behavior similar to those of poly(aniline). In addition, the boronic acid groups remain reactive, providing a chemical handle for further transformations. Substituted poly(aniline 3-boronic acid)s 6a can be similarly synthesized.

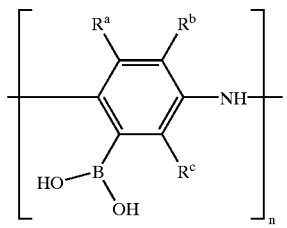

6a

Since the product is a polymer, it is understood that the poly(aniline boronic acid) precursor can also be poly(aniline 2-boronic acid), and will ultimately provide the same polymeric backbone. Accordingly, as used herein, the term poly(aniline boronic acid) is intended to mean poly(aniline 2-boronic acid) and poly(aniline 3-boronic acid).

Accordingly, one embodiment of the invention relates to a method of synthesizing a substituted poly(aniline) by reacting poly(aniline boronic acid) (optionally substituted with R$^a$, R$^b$ and R$^c$) with a reagent to produce a substituted poly(aniline) of formula I.

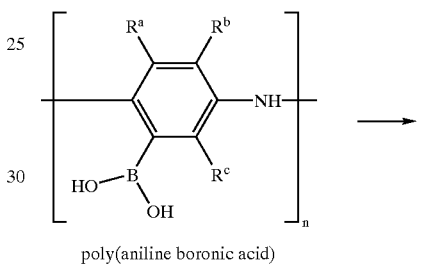

poly(aniline boronic acid)

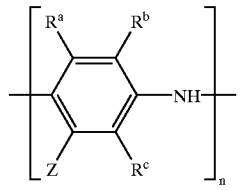

I

In formula I, n is an integer within the range of about 1–10,000,000, preferably within the range of about 3–5,000,000, and more preferably within the range of about 3–1,000,000. The Z substituent is produced by the reaction (e.g., oxidation, substitution, coupling) of the reagent and the boronic acid substituent.

In a preferred embodiment, the substituted aniline is a polymer (n>3). However, the invention also contemplates the synthesis of monomer substituted anilines (n=1) and dimer substituted anilines (n=2).

In another embodiment of the invention, each aniline has the same Z substituent. However, the methods of the invention also find utility in synthesizing poly(aniline)s where at least one of the Z substituents is boronic acid. This boronic acid-containing poly(aniline) is produced when the reaction is conducted so as to be an incomplete reaction, thus allowing some boronic acid substituents in the poly(aniline boronic acid) starting material to undergo an oxidation, substitution or cross-coupling reaction, while other boronic acid substituents remain unchanged. These remaining boronic acid substituents are particularly useful as cross-linking sites should it be desirable to cross-link the resulting polymer of formula I.

Accordingly, in one embodiment of the invention, a substituted poly(aniline) is synthesized by reacting poly (aniline boronic acid) with at least one reagent selected from the group consisting of oxidation reagents, ipso-substitution reagents, and cross-coupling reagents; stopping the reaction before all of the boronic acid substituents in the poly(aniline boronic acid) undergo oxidation, substitution or cross-coupling; to produce a substituted poly(aniline) of formula I':

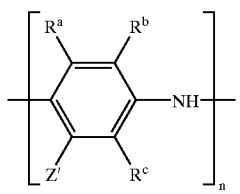

where n, $R^a$, $R^b$ and $R^c$ are as defined above; and wherein each Z' is independently selected from the group consisting of $-B(OH)_2$ and substituents produced by the reaction of the reagent and the boronic acid substituent, with the proviso that at least one Z' substituent is a substituent produced by the reaction of the reagent and the boronic acid substituent.

The methods also find utility in synthesizing poly (aniline)s where the Z substituents are varied. In this manner, each substituted aniline monomeric unit contains a Z substituent that may be the same or different from the Z substituent present in the adjacent monomeric unit. For example, after the forced termination of the transformation of boronic groups to Z with a specific reagent A, the leftover boronic groups can be converted to other Z groups with a different reagent B. Alternately, each boronic group can be converted to a different substituent group in the presence of different reagents. In this case, each substituent group is specifically produced from its respective reagent.

Accordingly, in another embodiment of the invention, a substituted poly(aniline) is synthesized by reacting poly (aniline boronic acid) with at least one reagent selected from the group consisting of oxidation reagents, ipso-substitution reagents, and cross-coupling reagents; to produce a substituted poly(aniline) of formula I, where n, R$a$, $R^b$ and $R^c$ are as defined above; and wherein each Z is the same or different and is a substituent produced by the reaction of the reagent and the boronic acid substituent.

Exemplary reagents include, by way of illustration and not limitation, oxidation reagents, ipso-substitution reagents, and cross-coupling reagents. These reagents can be either electrophilic or nucleophilic reagents, and some reagents may be classified under several categories. For example, $Br_2$ can functions as both an oxidation reagent and as an ipso-halogenation reagent.

Exemplary oxidation reactants include, by way of illustration and not limitation, peroxide.

Exemplary ipso-substitution reagents include, by way of illustration and not limitation, ipso-halogenation reagents, $HgCl_2$, and ipso-nitration reagents. Examples of ipso-halogenation reagents include molecular halogen. Examples of ipso-nitration reagents include $NH_4NO_3$.

Exemplary cross-coupling reagents include, by way of illustration and not limitation, $R^1$—SH, where $R^1$ is selected from the group consisting of —H, $-B(OH)_2$, alkyl, cycloalkyl, cycloheteroalkyl, aryl, heteroaryl and silyl; $R^2$—C≡C—$R^3$, where $R^2$ and $R^3$ are independently selected from the group consisting of —H, $-B(OH)_2$, alkyl, cycloalkyl, cycloheteroalkyl, aryl, heteroaryl and silyl; $R^4$—C(O)-thiophenyl, where $R^4$ is selected from the group consisting of —H, $-B(OH)_2$, alkyl, cycloalkyl, cycloheteroalkyl, aryl, heteroaryl and silyl; Suzuki cross-coupling reagents (e.g., $R^5$ substituted, halo-substituted benzene, where $R^5$ is selected from the group consisting of —H, $-B(OH)_2$, alkyl, cycloalkyl, cycloheteroalkyl, aryl, heteroaryl and silyl); and HO—C($R^5$)($R^6$)—C($R^7$)($R^8$)—OH, where $R^5$, $R^6$, $R^7$ and $R^8$ are independently selected from the group consisting of —H, $-B(OH)_2$, alkyl, cycloalkyl, cycloheteroalkyl, aryl, heteroaryl and silyl.

As noted in the background section, (hydroxyaniline) 4 is produced by the oxidative polymerization of its monomer. However, a variety of products is ultimately produced due to undesirable side-reactions. By using PABA 6 as the starting material, it is now possible to generate 4 exclusively in the presence of peroxide.

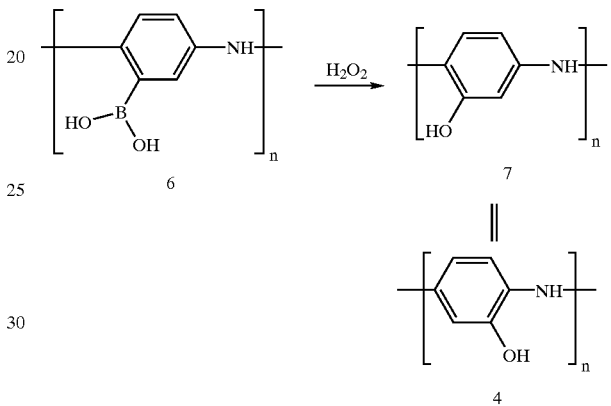

Accordingly, one embodiment of the invention relates to a method of synthesizing a hydroxy-substituted poly (aniline) by reacting poly(aniline 3-boronic acid) 6 with an oxidation reagent such as peroxide to produce a compound of formula Ia, where n is as defined above (formula Ia=formula I where Z is —OH). This is illustrated in the following Scheme Ia and in Example 2:

Scheme Ia

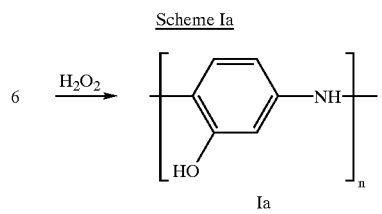

Details of this hydroxylation reaction, as well as those described below can be found in the references noted for Schemes 1–9.

Another embodiment of the invention relates to an ipso-halogenation reaction, whereby poly(aniline 3-boronic acid) 6 is reacted with molecular halogen (e.g., $Cl_2$, $Br_2$ or $I_2$) to produce a halo-substituted poly(aniline) of formula Ib, where n is as defined above (formula Ib=formula I where Z is a halo group such as —Cl, —Br or —I). This is illustrated in the following Scheme Ib and Examples 2 and 3:

Scheme Ib

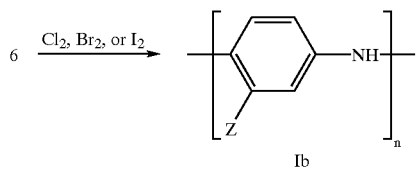

Scheme Ib is a significant advancement in the art since halogen-substituted poly(aniline)s Ib are difficult to synthesize using standard approaches, as noted in the background section. By using the poly(aniline 3-boronic acid) 6 of the invention, a range of halogenated poly(aniline)s Ib can be formed simply by exposing 6 to the corresponding molecular halogen in solution.

The invention also provides a coupling reaction for the synthesis of a thiol-substituted poly(aniline) by reacting poly(aniline 3-boronic acid) 6 with a thiol-containing compound ($R^1$—SH) to produce a compound of formula Ic (formula I where n is as defined above, and Z is —$SR^1$, where $R^1$ is selected from the group consisting of —H, —$B(OH)_2$, alkyl, cycloalkyl, cycloheteroalkyl, aryl, heteroaryl and silyl. This reaction is illustrated in the following Scheme Ic:

Scheme Ic

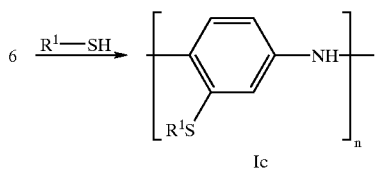

Another embodiment of the invention relates to a transmetallation reaction, whereby poly(aniline 3-boronic acid) 6 is reacted with $HgCl_2$ to produce an HgCl-substituted poly(aniline) of formula Id, where n is as defined above (formula Id=formula I where Z is —HgCl). This is illustrated in the following Scheme Id:

Scheme Id

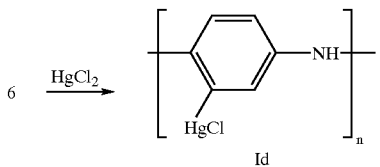

Another embodiment of the invention relates to a thioalkyne cross-coupling reaction, whereby a substituted poly(aniline) is prepared by reacting poly(aniline 3-boronic acid) 6 with a cross-coupling thioalkyne reagent of the formula $R^2$—C≡C—$R^3$, where $R^2$—C≡C—$R^3$, where $R^2$ and $R^3$ are independently selected from the group consisting of —H, —$B(OH)_2$, alkyl, cycloalkyl, cycloheteroalkyl, aryl, heteroaryl and silyl. The product is an alkyne-substituted poly(aniline) of formula Ie, where n is as defined above (formula Ie=formula I where Z is —C≡C—$R^3$). This reaction is illustrated in the following Scheme Ie:

Scheme Ie

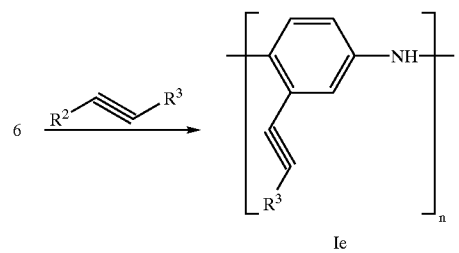

Another embodiment of the invention relates to a cross-coupling reaction, where poly(aniline 3-boronic acid) 6 is reacted with a cross-coupling thiol ester reagent to produce a carbonyl-substituted poly(aniline) of formula If, where n is as defined above (formula If=formula I where Z is —C(O)—$R^4$, where $R^4$ is selected from the group consisting of —H, —$B(OH)_2$, alkyl, cycloalkyl, cycloheteroalkyl, aryl, heteroaryl and silyl. This is illustrated in the following Scheme If:

Scheme If

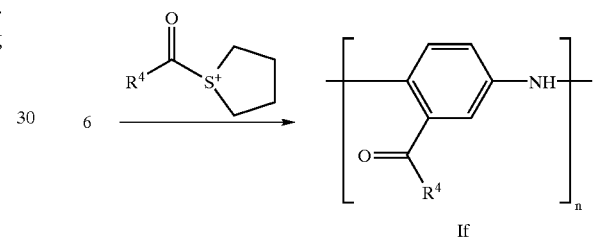

The invention also provides for a Suzuki cross-coupling reaction., whereby a substituted poly(aniline) is produced by reacting poly(aniline 3-boronic acid) 6 with a Suzuki cross-coupling reagent such as an $R^5$ substituted, halo-substituted benzene, where the halo group (X) can be chloro, bromo or iodo; and $R^5$ is selected from the group consisting of —H, —$B(OH)_2$, alkyl, cycloalkyl, cycloheteroalkyl, aryl, heteroaryl and silyl. The product is an aromatic-substituted poly(aniline) of formula Ig, where n is as defined above (formula Ig=formula I where Z is —$C_6H_5$—$R^5$). This is illustrated in the following Scheme Ig:

Scheme Ig

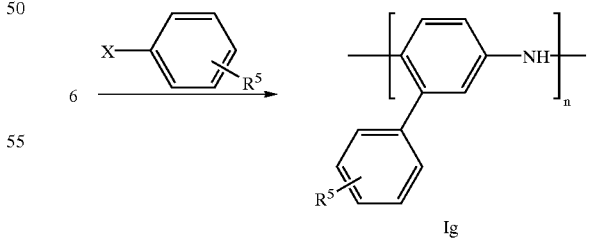

The invention also provides for a cyclic boron group as a protection group or as a possible precursor to an anionic boronate group, for the synthesis of organoborane compounds. Poly(aniline 3-boronic acid) 6 is reacted with HO—$C(CH_3)_2$—$C(CH_3)_2$—OH to produce a borane-substituted poly(aniline) of formula Ih, where n is as defined above (formula Ih=formula I where Z is a boron ester. An exemplary reagent is HO—C(CH$_3$)$_2$—C(CH$_3$)$_2$—OH, as illustrated in the following Scheme Ih:

Scheme Ih

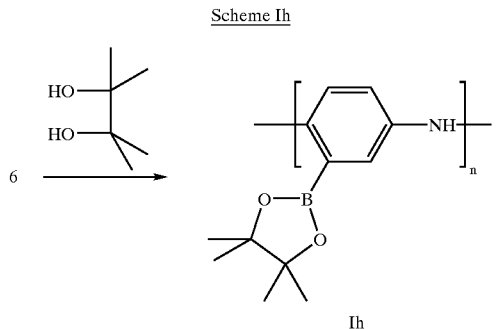

Another embodiment of the invention relates to an ipso-nitration reaction, whereby a substituted poly(aniline) is prepared by reacting poly(aniline 3-boronic acid) 6 with an ipso-nitration reagent such as ammonium nitrate to produce a nitro-substituted poly(aniline) of formula Ii, where n is as defined above (formula Ii=formula I where Z is —NO$_2$. This is illustrated in the following Scheme Ii:

Scheme Ii

The reactions illustrated in Schemes Ia–Ii are intended to be illustrative only, and represent just a few of the many possible reactions accessible through the boronic acid group present in the poly(aniline boronic acid) precursor. One of skill in the art will readily appreciate that this precursor can be used in a variety of reactions to produce substituted poly(aniline)s. Schemes Ia–Ii illustrate poly(aniline)s that are substituted at the three position, since the poly(aniline boronic acid) exemplified is poly(aniline 3-boronic acid). It is understood that 2-substituted poly(aniline)s are obtainable in the same manner, using the poly(aniline 2-boronic acid) precursor. Further, Schemes Ia–Ii illustrate poly(aniline)s having hydrogen as the R$^a$, R$^b$ and R$^c$ substituents. This is not intended to be limiting in any manner and poly(aniline)s having other R$^a$, R$^b$ and R$^c$ substituents can be readily synthesized by techniques that are known in the art.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature. See, for example, Kirk-Othmer's *Encyclopedia of Chemical Technology;* and House's *Modern Synthetic Reactions.*

The following examples are put forth so as to provide those of ordinary skill in the art with a complete disclosure and description of how to practice the methods of the invention. Efforts have been made to ensure accuracy with respect to numbers (e.g., amounts, temperature, etc.) but some experimental error and deviations should, of course, be allowed for. Unless indicated otherwise, parts are parts by weight, temperature is degrees centigrade and pressure is at or near atmospheric. All components were obtained commercially unless otherwise indicated.

| ABBREVIATIONS | |
| --- | --- |
| ABA | 3-aminophenylboronic acid |
| CV | cyclic voltammetry |
| GC electrodes | glassy carbon electrodes |
| PABA | poly(aniline-3-boronic acid) |
| RT | room temperature (~25° C.) |

MATERIALS AND METHODS

Reagents

ABA, bromine and iodine were purchased from Aldrich. Hydrogen peroxide (H$_2$O$_2$, 30%) and hydrochloric acid (conc.) were purchased from EM Science. The water that was used for all experiments was purified and deionized (18.3 MΩ). All chemicals were used as received.

Instrumental Setup

GC electrodes (3 mm diameter) were purchased from Bioanalytical Science. CV was performed with a potentiostat (EG&G Model: 362). In the voltammetric experiments, a three-electrode configuration was used including a platinum wire (length: 50 cm, diameter: 0.2 mm) counter electrode and a Ag/AgCl reference electrode. XPS spectra were recorded with an M-Probe surface spectrometer (Surface Science Instruments). All spectra were recorded with focused and monochromatized Al Kα$_{1,2}$ irradiation (hv=1486.6 eV), and the X-ray beam was incident on the surface at an angle of 55° with respect to the surface normal. All binding energies (BE) were referenced to the aromatic C1s peak, which was assigned a value of 284.7 eV according to the protocol described in Beamson et al., "High Resolution XPS of Organic Polymers: The Scienta ESCA300 Database" (Wiley and Sons, Chichester, 1992).

Example 1

PABA deposition

The oxidative polymerization of ABA 5 was performed producing PABA 6 as follows: ABA 5 (40 mM) and sodium fluoride (200 mM) were dissolved in 25 mL 0.5 M aqueous HCl. The potential of the GC electrode was scanned between 0.0 and 1.1 V vs. Ag/AgCl at a scan rate of 100 mV/s, and then polymerization was halted at +0.8 V when the charge passed for the reduction of the deposited polymer reached 0.34 mC. The PABA film had a deep greenish blue color similar to that obtained upon the formation of poly(aniline). After careful washing of the film with pure water, the electrode was soaked in 0.5 M HCl.

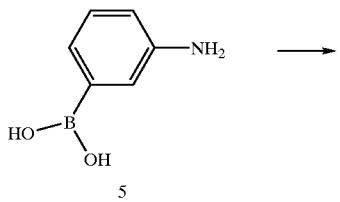

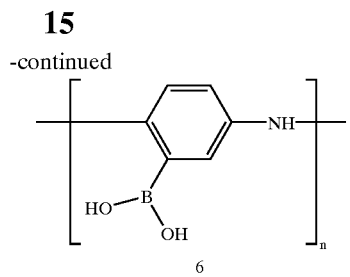

6

Example 2

Transformation from PABA to poly(hydroxyaniline) Ia

A beaker was charged with 3 mL $H_2O_2$ (30%) containing 0.5 M HCl. The PABA 6 electrode was dipped in the solution for 10 minutes at RT. The color of the film turned from green to deep blue. The reaction producing poly (hydroxyaniline) Ia was monitored frequently throughout the course of the transformation with CV in 0.5 M HCl by scanning within a potential window of −0.3 to +0.6 V vs. Ag/AgCl at a scan rate of mV/sec. After careful washing of the layer with pure water, the electrode was stored in 0.5 M HCl.

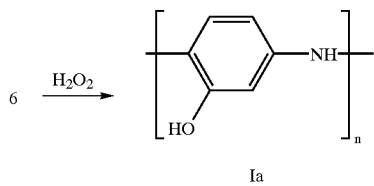

Ia

The observed voltammetry of the redox behavior of 6 before and after the reaction with peroxide, showing the conversion of 6 to Ia is similar to that reported for the polymer produced by the electrochemical oxidative polymerization of 1 (Cohen, et al., *Tetrahedron Lett.* 3555–3558 (1974), Cohen, et al., *J. Am. Chem. Soc.* 88, 4521–4522 (1966), and Nicolas, et al., *Eur. J. Org. Chem.* 9:1703–1710 (2000)).

The formation of 4 from electrochemically generated thin films of PABA 6 is further supported by FT-IR results, which show the growth of an intense peak at 1220 cm$^{-1}$ assigned to the C—O stretching associated with the formation of phenol. A broad peak at approximately 3300 cm$^{-1}$ indicates O—H stretching with strong inter-molecular hydrogen bonding, observed with polyhydroxy compounds (Lin-Vien, et al., *The Handbook of Infrared and Raman Characteristic Frequencies of Organic Molecules;* Academic Press: New York, 1991). According to the ipso-substitution mechanism (Taylor, R. *Electrophilic Aromatic Substitution,* Wiley: Chichester, 1990; Perrin, *J. Org. Chem.* 36:420 (1971); and Perrin, et al., J. Am. Chem. Soc. 93:3389 (1971)) and spectroscopic analysis, these results suggest that a single, linear structure 4 can be generated using boronic acid as the precursor.

Example 3

Transformation from PABA to poly(iodoaniline) Ib (Z=I)

The reaction conditions used were the same as those reported in Kuivila, et al., *J. Org. Chem.* 76:2679–2682 (1954). A stock solution was made by dissolving iodine (101.5 mg, 4 mM), sodium acetate (1.969 g, 0.24 M), and acetic acid (2.17 g, 0.361 M), in 100 mL of an aqueous solution containing 5% methanol. The freshly made PABA electrode was dipped in the solution (5 mL) for 50 minutes at RT. The reaction was monitored frequently throughout the course of the transformation with CV in 0.5 M HCl by scanning within a potential window of 0.0 to +0.8 V vs. Ag/AgCl at a scan rate of 100 mV/sec.

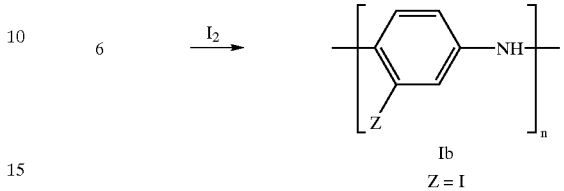

Z = I

Example 4

Transformation from PABA to poly(bromoaniline) Ib (Z=Br)

The reaction conditions used were the same as those reported in Kuivila, et al., *J. Org. Chem.* 73: 4629–4632 (1951). A stock solution was made by dissolving bromine (320 mg, 20 mM) in 100 mL 50 wt % acetic acid aqueous solution. The freshly made PABA electrode was dipped in the solution (5 mL) for 10 minutes at RT. The reaction was monitored frequently throughout the course of the transformation with CV in 0.5 M HCl by scanning within a potential window of 0.0 to +0.8 V vs. Ag/AgCl at a scan rate of 100 mV/sec.

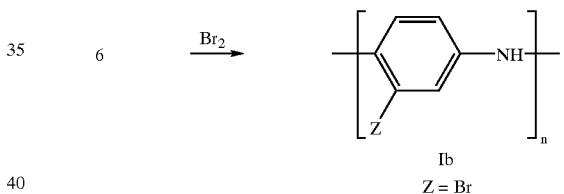

Z = Br

The observed voltammetry of the redox behavior of 6 before and after the reaction with molecular bromine, showing the conversion of 6 to Ib (Z=Br) is similar to that reported for the same polymer created electrochemically from 2-bromoaniline (Prasad, et al., *J. Polym. Mater.* 13:305–311 (1996)). High-resolution X-ray photo-electron spectra in the $N_{1s}$ region exhibited a peak near 400 eV with the major component at a binding energy of 399.7 eV, which is characteristic of amine —NH-nitrogen. An additional component was observed at 400.9 eV that corresponds to the positively charged N$^+$nitrogen typically observed for poly (aniline) (Lim, et al., *Langmuir* 14:5305–5313 (1998) and Neoh, et al., *Chem. Mater.* 9:2906–2912 (1997)). A clear doublet was observed at 71.9 and 70.8 eV, which corresponds to Br $3d_{3/2}$ and $3d_{5/2}$, respectively, and is attributed to the presence of C—Br (From data observed for poly(4-bromostyrene) in: Beamson, et al., *High-Resolution XPS of Organic Polymers: The Scienta ESCA300 Database,* page 274, Wiley and Sons, Chichester, 1992).

All patents, publications, and other published documents mentioned or referred to herein are incorporated by reference in their entireties.

It is to be understood that while the invention has been described in conjunction with the preferred specific embodiments thereof, that the foregoing description as well as the examples that follow, are intended to illustrate and not limit the scope of the invention. It should be understood by those skilled in the art that various changes may be made and equivalents may be substituted without departing from the scope of the invention, and further that other aspects, advantages and modifications will be apparent to those skilled in the art to which the invention pertains.

We claim:

1. A method of synthesizing a substituted poly(aniline), comprising:

reacting poly(aniline boronic acid) with a reagent to produce a substituted poly(aniline) of formula I:

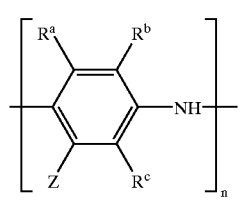

where n is an integer within the range of about 1–10,000,000; $R^a$, $R^b$ and $R^c$ are independently selected from the group consisting of —H, alkyl, —B(OH)$_2$, cycloalkyl, cycloheteroalkyl, aryl, heteroaryl and silyl; and Z is a substituent produced by the reaction of the reagent and the boronic acid substituent.

2. The method of claim 1 wherein n is an integer within the range of about 3–5,000,000.

3. The method of claim 2 wherein n is an integer within the range of about 3–1,000,000.

4. The method of claim 1 wherein the reagent is selected from the group consisting of oxidation reagents, ipso-substitution reagents, and cross-coupling reagents.

5. The method of claim 4 wherein the reagent is an oxidation reagent.

6. The method of claim 5 wherein the oxidation reagent is peroxide.

7. The method of claim 4 wherein the ipso-substitution reagent is selected from the group consisting of ipso-halogenation reagents, HgCl$_2$, and ipso-nitration reagents.

8. The method of claim 7 wherein the ipso-halogenation reagent is a molecular halogen.

9. The method of claim 7 wherein the ipso-substitution reagent is HgCl$_2$.

10. The method of claim 7 wherein the ipso-nitration reagent is NH$_4$NO$_3$.

11. The method of claim 4 wherein the reagent is a cross-coupling reagent.

12. The method of claim 11 wherein the cross-coupling reagent is R$^1$—SH, where R$^1$ is selected from the group consisting of —H, —B(OH)$_2$, alkyl, cycloalkyl, cycloheteroalkyl, aryl, heteroaryl and silyl.

13. The method of claim 11 wherein the cross-coupling reagent is R$^2$—C≡C—R$^3$, where R$^2$ and R$^3$ are independently selected from the group consisting of —H, —B(OH)$_2$, alkyl, cycloalkyl, cycloheteroalkyl, aryl, heteroaryl and silyl.

14. The method of claim 11 wherein the cross-coupling reagent is R$^4$—C(O)-thiophenyl, where R$^4$ is selected from the group consisting of —H, —B(OH)$_2$, alkyl, cycloalkyl, cycloheteroalkyl, aryl, heteroaryl and silyl.

15. The method of claim 11 wherein the cross-coupling reagent is a Suzuki cross-coupling reagent.

16. The method of claim 15 wherein the Suzuki cross-coupling reagent is an R$^5$ substituted, halo-substituted benzene, where R$^5$ is selected from the group consisting of —H, —B(OH)$_2$, alkyl, cycloalkyl, cycloheteroalkyl, aryl, heteroaryl and silyl.

17. The method of claim 11 wherein the cross-coupling reagent is HO—C(R$^5$)(R$^6$)—C(R$^7$)(R$^8$)—OH, where R$^5$, R$^6$, R$^7$ and R$^8$ are independently selected from the group consisting of —H, —B(OH)$_2$, alkyl, cycloalkyl, cycloheteroalkyl, aryl, heteroaryl and silyl.

18. A method of synthesizing a substituted poly(aniline), comprising:

reacting poly(aniline 3-boronic acid) with at least one reagent selected from the group consisting of oxidation reagents, ipso-substitution reagents, and cross-coupling reagents;

to produce a substituted poly(aniline) of formula I:

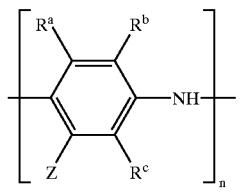

where n is an integer within the range of about 1–10,000,000; $R^a$, $R^b$ and $R^c$ are independently selected from the group consisting of —H, alkyl, —B(OH)$_2$, cycloalkyl, cycloheteroalkyl, aryl, heteroaryl and silyl; and Z is a substituent produced by the reaction of the reagent and the boronic acid substituent.

19. The method of claim 18 wherein n is an integer within the range of about 3–5,000,000.

20. The method of claim 19 wherein n is an integer within the range of about 3–1,000,000.

21. The method of claim 18 wherein the oxidation reagent is peroxide.

22. The method of claim 18 wherein the ipso-substitution reagent is selected from the group consisting of ipso-halogenation reagents, HgCl$_2$, and ipso-nitration reagents.

23. The method of claim 22 wherein the ipso-halogenation reagent is a molecular halogen.

24. The method of claim 23 wherein the molecular halogen is selected from the group consisting of Cl$_2$, Br$_2$, and I$_2$.

25. The method of claim 22 wherein the ipso-substitution reagent is HgCl$_2$.

26. The method of claim 22 wherein the ipso-nitration reagent is NH$_4$NO$_3$.

27. The method of claim 18 wherein the cross-coupling reagent is R$^1$—SH, where R$^1$ is selected from the group consisting of —H, —B(OH)$_2$, alkyl, cycloalkyl, cycloheteroalkyl, aryl, heteroaryl and silyl.

28. The method of claim 18 wherein the cross-coupling reagent is R$^2$—C≡C—R$^3$, where R$^2$ and R$^3$ are independently selected from the group consisting of —H, —B(OH)$_2$, alkyl, cycloalkyl, cycloheteroalkyl, aryl, heteroaryl and silyl.

29. The method of claim 18 wherein the cross-coupling reagent is R$^4$—C(O)-thiophenyl, where R$^4$ is selected from the group consisting of —H, —B(OH)$_2$, alkyl, cycloalkyl, cycloheteroalkyl, aryl, heteroaryl and silyl.

30. The method of claim 18 wherein the cross-coupling reagent is a Suzuki cross-coupling reagent.

31. The method of claim 30 wherein the Suzuki cross-coupling reagent is an R$^5$ substituted, halo-substituted benzene, where R$^5$ is selected from the group consisting of —H, —B(OH)$_2$, alkyl, cycloalkyl, cycloheteroalkyl, aryl, heteroaryl and silyl.

32. The method of claim 18 wherein the cross-coupling reagent is HO—C(R$^5$)(R$^6$)—C(R$^7$)(R$^8$)—OH, where R$^5$, R$^6$, R$^7$ and R$^8$ are independently selected from the group consisting of —H, —B(OH)$_2$, alkyl, cycloalkyl, cycloheteroalkyl, aryl, heteroaryl and silyl.

33. A method of synthesizing a substituted poly(aniline) comprising:

reacting poly(aniline boronic acid) with at least one reagent selected from the group consisting of oxidation reagents, ipso-substitution reagents, and cross-coupling reagents;

stopping the reaction before all of the boronic acid substituents in the poly(aniline boronic acid) undergo oxidation, substitution or cross-coupling;

to produce a substituted poly(aniline) of formula I':

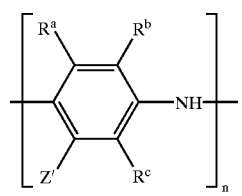

I' where n is an integer within the range of about 1–10,000,000; R$^a$, R$^b$ and R$^c$ are independently selected from the group consisting of —H, alkyl, —B(OH)$_2$, cycloalkyl, cycloheteroalkyl, aryl, heteroaryl and silyl; and wherein each Z' is independently selected from the group consisting of —B(OH)$_2$ and substituents produced by the reaction of the reagent and the boronic acid substituent, with the proviso that at least one Z' substituent is a substituent produced by the reaction of the reagent and the boronic acid substituent.

34. The method of claim 33 wherein the oxidation reagent is peroxide.

35. The method of claim 33 wherein the ipso-substitution reagent is selected from the group consisting of ipso-halogenation reagents, HgCl$_2$, and ipso-nitration reagents.

36. The method of claim 33 wherein the cross-coupling reagent is selected from the group consisting of R$^1$—SH, where R$^1$ is selected from the group consisting of —H, —B(OH)$_2$, alkyl, cycloalkyl, cycloheteroalkyl, aryl, heteroaryl and silyl; R$^2$—C≡C—R$^3$, where R$^2$ and R$^3$ are independently selected from the group consisting of —H, —B(OH)$_2$, alkyl, cycloalkyl, cycloheteroalkyl, aryl, heteroaryl and silyl; R$^4$—C(O)-thiophenyl, where R$^4$ is selected from the group consisting of —H, —B(OH)$_2$, alkyl, cycloalkyl, cycloheteroalkyl, aryl, heteroaryl and silyl; an R$^5$ substituted, halo-substituted benzene, where R$^5$ is selected from the group consisting of —H, —B(OH)$_2$, alkyl, cycloalkyl, cycloheteroalkyl, aryl, heteroaryl and silyl; and HO—C(R$^5$)(R$^6$)—C(R$^7$)(R$^8$)—OH, where R$^5$, R$^6$, R$^7$ and R$^8$ are independently selected from the group consisting of —H, —B(OH)$_2$, alkyl, cycloalkyl, cycloheteroalkyl, aryl, heteroaryl and silyl.

37. A method of synthesizing a substituted poly(aniline) comprising:

reacting poly(aniline boronic acid) with at least one reagent selected from the group consisting of oxidation reagents, ipso-substitution reagents, and cross-coupling reagents;

to produce a substituted poly(aniline) of formula I:

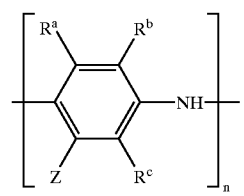

I where n is an integer within the range of about 1–10,000,000; R$^a$, R$^b$ and R$^c$ are independently selected from the group consisting of —H, alkyl, —B(OH)$_2$, cycloalkyl, cycloheteroalkyl, aryl, heteroaryl and silyl; and wherein each Z is the same or different and is a substituent produced by the reaction of the reagent and the boronic acid substituent.

38. The method of claim 37 wherein the oxidation reagent is peroxide.

39. The method of claim 37 wherein the ipso-substitution reagent is selected from the group consisting of ipso-halogenation reagents, HgCl$_2$, and ipso-nitration reagents.

40. The method of claim 37 wherein the cross-coupling reagent is selected from the group consisting of R$^1$—SH, where R$^1$ is selected from the group consisting of —H, —B(OH)$_2$, alkyl, cycloalkyl, cycloheteroalkyl, aryl, heteroaryl and silyl; R$^2$—C≡C—R$^3$, where R$^2$ and R$^3$ are independently selected from the group consisting of —H, —B(OH)$_2$, alkyl, cycloalkyl, cycloheteroalkyl, aryl, heteroaryl and silyl; R$^4$—C(O)-thiophenyl, where R$^4$ is selected from the group consisting of —H, —B(OH)$_2$, alkyl, cycloalkyl, cycloheteroalkyl, aryl, heteroaryl and silyl; an R$^5$ substituted, halo-substituted benzene, where R$^5$ is selected from the group consisting of —H, —B(OH)$_2$, alkyl, cycloalkyl, cycloheteroalkyl, aryl, heteroaryl and silyl; and HO—C(R$^5$)(R$^6$)—C(R$^7$)(R$^8$)—OH, where R$^5$, R$^6$, R$^7$ and R$^8$ are independently selected from the group consisting of —H, —B(OH)$_2$, alkyl, cycloalkyl, cycloheteroalkyl, aryl, heteroaryl and silyl.

* * * * *